United States Patent
Huber-Dirr et al.

(10) Patent No.: US 7,663,003 B2
(45) Date of Patent: Feb. 16, 2010

(54) CATALYST AND METHOD FOR THE HYDRATION OF CARBONYL COMPOUNDS

(75) Inventors: Sylvia Huber-Dirr, Zwingenberg (DE); Michael Hesse, Worms (DE); Andrea Haunert, Mannheim (DE); Henrik Junicke, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/937,537

(22) Filed: Nov. 9, 2007

(65) Prior Publication Data

US 2008/0064882 A1     Mar. 13, 2008

Related U.S. Application Data

(62) Division of application No. 10/549,140, filed as application No. PCT/EP2004/002929 on Mar. 20, 2004.

(30) Foreign Application Priority Data

Mar. 27, 2003  (DE) ............................... 103 13 702

(51) Int. Cl.
   *B01J 23/70*  (2006.01)
   *B01J 23/00*  (2006.01)
   *C07C 27/04*  (2006.01)
   *C07C 27/00*  (2006.01)
   *C07C 305/00* (2006.01)

(52) U.S. Cl. .................... 568/814; 568/861; 568/885; 568/903; 502/345; 502/346; 502/350; 549/263

(58) Field of Classification Search ............... 568/903, 568/885, 814, 861; 502/345, 346, 350; 549/263
   See application file for complete search history.

(56) References Cited

U.S. PATENT DOCUMENTS

| 3,923,694 A | | 12/1975 | Cornthwaite |
| 4,287,099 A | | 9/1981 | Baer et al. |
| 4,598,061 A | * | 7/1986 | Schneider et al. ........... 502/303 |
| 4,738,946 A | | 4/1988 | Yamashita et al. |
| 4,762,817 A | * | 8/1988 | Logsdon et al. ............. 502/329 |
| 5,475,159 A | | 12/1995 | Singleton et al. |
| 5,569,792 A | * | 10/1996 | Deckers et al. .............. 568/881 |
| 5,990,040 A | | 11/1999 | Hu et al. |
| 6,448,457 B1 | * | 9/2002 | Hesse et al. ................. 568/885 |
| 6,455,464 B1 | | 9/2002 | Chen |

FOREIGN PATENT DOCUMENTS

| DE | 256 515 | 7/1911 |
| DE | 195 05 347 | 9/1995 |
| DE | 196 07 954 | 9/1997 |
| DE | 196 07 955 | 9/1997 |
| DE | 196 47 348 | 5/1998 |
| DE | 196 47 349 | 5/1998 |
| DE | 198 09 418 | 9/1999 |

* cited by examiner

*Primary Examiner*—Taylor Victor Oh
(74) *Attorney, Agent, or Firm*—Oblon, Spivak, McClelland, Maier & Neustadt, L.L.P.

(57) ABSTRACT

A process for hydrogenating an organic compound which has at least one carbonyl group, in which the organic compound is brought into contact in the presence of hydrogen with a shaped article which can be produced in a process in which (i) an oxidic material comprising copper oxide, aluminum oxide and at least one of the oxides of lanthanum, tungsten, molybdenum, titanium or zirconium is prepared, (ii) powdered metallic copper, copper flakes, powdered cement, graphite or a mixture thereof is added to the oxidic material, and (iii) the mixture resulting from (ii) is shaped to a shaped article.

15 Claims, No Drawings

CATALYST AND METHOD FOR THE HYDRATION OF CARBONYL COMPOUNDS

The present invention relates to a process for hydrogenating organic compounds which have at least one carbonyl group using a catalyst which is distinguished inter alia in that it consists of copper oxide, aluminum oxide and at least one of the oxides of lanthanum, tungsten, molybdenum, titanium or zirconium and in that a catalyst with high selectivity and, at the same time, high stability is produced through the addition of oxides of lanthanum, tungsten, molybdenum, titanium or zirconium. In the preparation thereof it is possible additionally to add copper powder, copper flakes or cement. The present invention likewise relates to the catalyst per se and very generally to the use of lanthanum oxide in the preparation of catalysts with high selectivity and, at the same time, high stability.

The catalytic hydrogenation of carbonyl compounds such as, for example, carboxylic acids or carboxylic esters occupies an important position in the production sequences in the basic chemicals industry.

The catalytic hydrogenation of carbonyl compounds such as, for example, carboxylic esters is carried out in industrial processes almost exclusively in fixed bed reactors. The fixed bed catalysts used are, besides catalysts of the Raney type, especially supported catalysts, for example copper, nickel or noble metal catalysts.

U.S. Pat. No. 3,923,694 describes, for example, a catalyst of the copper oxide/zinc oxide/aluminum oxide type. The disadvantage of this catalyst is that it has insufficient mechanical stability during the reaction and therefore disintegrates relatively quickly. This results in a loss of activity and a build up of a difference in pressure across the reactor owing to the disintegrating catalyst shaped articles. It is consequently necessary to shut down the plant prematurely.

DE 198 09 418.3 describes a process for the catalytic hydrogenation of a carbonyl compound in the presence of a catalyst which comprises a support, which mainly contains titanium dioxide, and as active component copper or a mixture of copper with at least one of the metals selected from the group of zinc, aluminum, cerium, a noble metal and a group VII metal, where the copper surface area does not exceed 10 $m^2/g$. Preferred support materials are mixtures of titanium dioxide with aluminum oxide or zirconium oxide or aluminum oxide and zirconium oxide. In a preferred embodiment, the catalyst material is shaped with addition of metallic copper powder or copper flakes.

DE-A 195 05 347 describes very generally a process for preparing catalyst tablets of high mechanical strength, where a metal powder or a powder of a metal alloy is added to the material to be tableted. The metal powder added is, inter alia, aluminum powder or copper powder or copper flakes. However, on addition of aluminum powder in the case of a copper oxide/zinc oxide/aluminum oxide catalyst, the resulting shaped article has a side crushing strength which is worse than that of a shaped article prepared without addition of aluminum powder, and the shaped article of the invention showed, when used as catalyst, a conversion activity which was less than that of catalysts pre-pared without addition of aluminum powder. Likewise disclosed therein is a hydrogenation catalyst composed of NiO, $ZrO_2$, $MoO_3$ and CuO, to which Cu powder inter alia was admixed during the preparation. However, no statements are made in this publication about the selectivity or the activity.

DE 256 515 describes a process for preparing alcohols from synthesis gas, employing catalysts based on Cu/Al/Zn which are obtained by grinding and pelletizing together with metallic copper powder or copper flakes. The main object of the described process is to prepare mixtures of C1 to C5 alcohols, the process being managed in such a way that the upper third of the layer in the reactor contains a catalyst which has a higher content of copper powder or copper flakes, and the lower third contains a catalyst which has a lower content of copper powder or copper flakes.

It is an object of the present invention to provide a process and a catalyst which do not have the prior art disadvantages and to provide processes for the catalytic hydrogenation of carbonyl compounds, and catalysts, where the catalysts have both high mechanical stability and high hydrogenation activity and selectivity.

We have found that this object is achieved by simultaneous precipitation of copper compound, aluminum compound and at least one lanthanum, tungsten, molybdenum, titanium or zirconium compound and by subsequent drying, calcination, tableting and by addition of metallic copper powder, copper flakes or cement powder or graphite or a mixture, resulting in a catalyst which leads through the addition of at least one lanthanum, tungsten, molybdenum, titanium or zirconium compound both to high activities and selectivities and to high stability of the shaped article employed as catalyst.

Accordingly, the present invention relates to a process for hydrogenating an organic compound which has at least one carbonyl group, in which the organic compound is brought into contact in the presence of hydrogen with a shaped article which can be produced in a process in which (i) an oxidic material comprising copper oxide, aluminum oxide and at least one of the oxides of lanthanum, tungsten, molybdenum, titanium or zirconium is prepared, (ii) powdered metallic copper, copper flakes, powdered cement or graphite or a mixture thereof can be added to the oxidic material, and (iii) the mixture resulting from (ii) is shaped to a shaped article.

Of the oxides of lanthanum, tungsten, molybdenum, titanium or zirconium, preference is given to lanthanum oxide.

In preferred embodiments, the shaped articles of the invention are employed as unsupported, impregnated, coated and precipitated catalysts.

The catalyst used in the process of the invention is distinguished by the copper active component, aluminum component and the component of at least one of the oxides of lanthanum, tungsten, molybdenum, titanium or zirconium preferably being precipitated simultaneously or successively with a sodium carbonate solution, followed by drying, calcination, tableting and again calcination.

The following precipitation method is particularly suitable:

A) A copper salt solution, an aluminum salt solution and a solution of at least one salt of lanthanum, tungsten, molybdenum, titanium or zirconium, or a solution containing copper, aluminum and at least one of the salts of lanthanum, tungsten, molybdenum, titanium or zirconium, is precipitated in parallel or successively with a sodium carbonate solution. The precipitated material is subsequently dried and, where appropriate, calcined.

B) Precipitation of a copper salt solution and of a solution of at least one salt of lanthanum, tungsten, molybdenum, titanium or zirconium or of a solution containing copper salt and at least one salt of lanthanum, tungsten, molybdenum, titanium or zirconium, on a prefabricated aluminum oxide support. In a particularly preferred embodiment, the latter is in the form of a powder in an aqueous suspension. The support material may, however, also be in the form of beads, pellets, chips or tablets.

B1) In one embodiment (I), a copper salt solution and a solution of at least one salt of lanthanum, tungsten, molybdenum, titanium or zirconium, or a solution containing copper salt and at least one salt of lanthanum, tungsten, molybdenum, titanium or zirconium, is precipitated, preferably with sodium carbonate solution. An aqueous suspension of the aluminum oxide support material is present in the recipient vessel.

Precipitates resulting from A) or B) are filtered in a conventional way and, preferably, washed free of alkali, as described, for example, in DE 198 09 418.3.

Both the final products from A) and those from B) are dried at temperatures of from 50 to 150° C., preferably at 120° C., and subsequently where appropriate calcined at, in general, 200 to 600° C., in particular at 300 to 500° C., preferably for 2 hours.

Starting substances which can be used for A) and/or B) are in principle all Cu(I) and/or Cu(II) salts which are soluble in the solvents used for the application, such as, for example, nitrates, carbonates, acetates, oxalates or ammonium complexes, analogous aluminum salts and salts of lanthanum, tungsten, molybdenum, titanium or zirconium. Copper nitrate is particularly preferably employed for process A) and B).

In the process of the invention, the dried and, where appropriate, calcined powder described above is preferably processed to tablets, rings, annular tablets, extrudates, honeycombs or similar shaped articles. Processes possible for this are all those suitable from the prior art.

The composition of the oxidic material is generally such that the content of copper oxide is in the range from 40 to 90% by weight, the content of oxides of lanthanum, tungsten, molybdenum, titanium or zirconium is in the range from 0 to 50% by weight and the content of aluminum oxide is in the range up to 50% by weight, in each case based on the complete weight of the total of the abovementioned oxidic constituents, these three oxides together representing at least 80% by weight of the oxidic material after calcination, where cement is not included with the oxidic material in the above sense.

In a preferred embodiment, the present invention therefore relates to a process as described above, wherein the oxidic material includes
(a) copper oxide with a content in the range of $50 \leq x \leq 80$, preferably $55 \leq x \leq 75$, % by weight,
(b) aluminum oxide with a content in the range of $15 \leq y \leq 35$, preferably $20 \leq y \leq 30$, % by weight and
(c) at least one of the oxides of lanthanum, tungsten, molybdenum, titanium or zirconium with a content in the range of $2 \leq z \leq 20$, preferably $3 \leq z \leq 15$, % by weight,
in each case based on the total weight of the oxidic material after calcination, where the following applies: $80 \leq x+y+z \leq 100$, in particular $95 \leq x+y+z \leq 100$.

The process of the invention and the catalysts of the invention are distinguished by the addition of lanthanum, tungsten, molybdenum, titanium or zirconium in the precipitation leading to a high stability of the shaped article employed as catalyst.

In general, powdered copper, copper flakes or powdered cement or graphite or a mixture thereof is added in the range from 1 to 40% by weight, preferably in the range from 2 to 20% by weight and particularly preferably in the range from 3 to 10% by weight, in each case based on the total weight of the oxidic material, to the oxidic material.

The cement preferably employed is a high-alumina cement. The high-alumina cement particularly preferably consists essentially of aluminum oxide and calcium oxide, and it particularly preferably consists of approximately 75 to 85% by weight aluminum oxide and approximately 15 to 25% by weight calcium oxide. Further possibilities are to use a cement based on magnesium oxide/aluminum oxide, calcium oxide/silicon oxide and calcium oxide/aluminum oxide/iron oxide.

In particular, the oxidic material may have a content not exceeding 10% by weight, preferably not exceeding 5% by weight, based on the total weight of the oxidic material, of at least one further component selected from the group consisting of the elements Re, Fe, Ru, Co, Rh, Ir, Ni, Pd and Pt.

In a further preferred embodiment of the process of the invention, graphite is added to the oxidic material before the shaping to the shaped article in addition to the copper powder, the copper flakes or the cement powder or the mixture thereof. The amount of graphite added is preferably such that the shaping to a shaped article can be carried out better. In a preferred embodiment, 0.5 to 5% by weight graphite, based on the total weight of the oxidic material, are added. It is immaterial in this connection whether graphite is added to the oxidic material before or after or simultaneously with the copper powder, the copper flakes or the cement powder or the mixture thereof.

Accordingly, the present invention also relates to a process as described above, wherein graphite is added in a content in the range from 0.5 to 5% by weight based on the total weight of the oxidic material to the oxidic material or to the mixture resulting from (ii).

In a preferred embodiment, the present invention therefore also relates to a shaped article comprising
an oxidic material which includes
(a) copper oxide with a content in the range of $50 \leq x \leq 80$, preferably $55 \leq x \leq 75$, % by weight,
(b) aluminum oxide with a content in the range of $15 \leq y \leq 35$, preferably $20 \leq y \leq 30$, % by weight and
(c) at least one of the oxides of lanthanum, tungsten, molybdenum, titanium or zirconium with a content in the range of $2 \leq z \leq 20$, preferably $3 \leq z \leq 15$, % by weight,
in each case based on the total weight of the oxidic material after calcination, where the following applies: $80 \leq x+y+z \leq 100$, in particular $95 \leq x+y+z \leq 100$,
metallic copper powder, copper flakes or cement powder or a mixture thereof with a content in the range from 1 to 40% by weight based on the total weight of the oxidic material, and
graphite with a content of from 0.5 to 5% by weight based on the total weight of the oxidic material,
where the total of the contents of oxidic material, metallic copper powder, copper flakes or cement powder or a mixture thereof and graphite accounts for at least 95% by weight of the shaped article.

After addition of the copper powder, of the copper flakes or of the cement powder or of the mixture thereof and, where appropriate, graphite to the oxidic material, the shaped article obtained following the shaping is, where appropriate, calcined at least once for a time of, in general, 0.5 to 10 h, preferably 0.5 to 2 hours. The temperature during this at least one calcination step is generally in the range from 200 to 600° C., preferably in the range from 250 to 500° C. and particularly preferably in the range from 270 to 400° C.

In the case of shaping with cement powder, it may be advantageous for the shaped article obtained before the calcination to be moistened with water and then to be dried.

On use as catalyst in the oxidic form, the shaped article is, before charging with the hydrogenation solution, pre-reduced with reducing gases, for example hydrogen, preferably hydrogen/inert gas mixtures, especially hydrogen/nitrogen mixtures, at temperatures in the range from 100 to 500° C., preferably in the range from 150 to 350° C. and in particular in the range from 180 to 200° C. It is preferred to use in this connection a mixture having a hydrogen content in the range from 1 to 100% by volume, particularly preferably in the range from 1 to 50% by volume.

In a preferred embodiment, the shaped article of the invention is activated by treatment with reducing media in a manner known per se before use as catalyst. The activation takes place either beforehand in a reducing furnace or after installation in the reactor. If the catalyst has been activated beforehand in the reducing furnace, it is installed in the reactor and immediately charged with the hydrogenation solution under a pressure of hydrogen.

The preferred area of use of the shaped articles prepared by the process of the invention is the fixed-bed hydrogenation of organic compounds having carbonyl groups. Other embodiments such as, for example, fluidized reaction with catalyst material in fluid motion up and down are, however, likewise possible. The hydrogenation can be carried out in the gas phase or in the liquid phase. The hydrogenation is preferably carried out in the liquid phase, for example in a downflow or upflow procedure.

With a downflow procedure, the liquid precursor containing the carbonyl compound to be hydrogenated is allowed to trickle over the catalyst bed arranged in the reactor, which is under a pressure of hydrogen, with a thin film of liquid forming on the catalyst. By contrast, with an upflow procedure, hydrogen gas is passed into the reactor through which the liquid reaction mixture flows, with the hydrogen passing through the catalyst bed in ascending gas bubbles.

In one embodiment, the solution to be hydrogenated is pumped straight through the catalyst bed. In another embodiment of the process of the invention, part of the product after passing through the reactor is continuously taken off as product stream and, where appropriate, passed through a second reactor as defined above. The other part of the product is fed to the reactor again together with fresh precursor containing the carbonyl compound. This procedure is referred to as recycle procedure below.

If the downflow procedure is chosen as embodiment of the process of the invention, the recycle procedure is preferred. It is further preferred to use a main reactor and second reactor in the recycle procedure.

The process of the invention is suitable for the hydrogenation of carbonyl compounds such as aldehydes and ketones, carboxylic acids, carboxylic esters or carboxylic anhydrides to the corresponding alcohols, with aliphatic and cycloaliphatic, saturated and unsaturated carbonyl compounds being preferred. With aromatic carbonyl compounds there may be formation of unwanted by-products through hydrogenation of the aromatic nucleus. The carbonyl compounds may contain other functional groups such as hydroxyl or amino groups. Unsaturated carbonyl compounds are usually hydrogenated to the corresponding saturated alcohols. The term "carbonyl compounds" as used for the purpose of the invention comprises all compounds which have a C=O group, including carboxylic acids and derivatives thereof. It is, of course, also possible to hydrogenate mixtures of two or more than two carbonyl compounds together. A further possibility is also for the individual carbonyl compound to be hydrogenated to contain more than one carbonyl group.

The process of the invention is preferably employed for hydrogenating aliphatic aldehydes, hydroxy aldehydes, ketones, acids, esters, anhydrides, lactones and sugars.

Preferred aliphatic aldehydes are branched and unbranched, saturated and/or unsaturated aliphatic $C_2$-$C_{30}$-aldehydes like those obtainable, for example, by oxo synthesis from linear or branched olefins with internal or terminal double bond. A further possibility is also to hydrogenate oligomeric compounds which also contain more than 30 carbonyl groups.

Examples of aliphatic aldehydes which may be mentioned are:

formaldehyde, propionaldehyde, n-butyraldehyde, isobutyraldehyde, valeraldehyde, 2-methylbutyraldehyde, 3-methylbutyraldehyde (isovaleraldehyde), 2,2-dimethyl-propionaldehyde (pivalaldehyde), caproaldehyde, 2-methylvaleraldehyde, 3-methylvaleraldehyde, 4-methylvaleraldehyde, 2-ethylbutyraldehyde, 2,2-dimethyl-butyraldehyde, 3,3-dimethylbutyraldehyde, caprylaldehyde, capraldehyde, glutaraldehyde.

Besides the short-chain aldehydes mentioned, also particularly suitable are long-chain aliphatic aldehydes like those which can be obtained, for example, by oxo synthesis from linear α-olefins.

Enalization products are particularly preferred, such as 2-ethylhexenal, 2-methylpentenal, 2,4-diethyloctenal or 2,4-dimethylheptenal.

Preferred hydroxy aldehydes are $C_3$-$C_{12}$-hydroxy aldehydes like those obtainable, for example, by aldol reaction from aliphatic and cycloaliphatic aldehydes and ketones with themselves or formaldehyde. Examples are 3-hydroxypropanal, dimethylolethanal, trimethylolethanal (pentaerythrital), 3-hydroxybutanal (acetaldol), 3-hydroxy-2-ethylhexanal (butyraldol), 3-hydroxy-2-methylpentanal (propionaldol), 2-methylol-propanal, 2,2-dimethylolpropanal, 3-hydroxy-2-methylbutanal, 3-hydroxypentanal, 2-methylolbutanal, 2,2-dimethylolbutanal, hydroxypivalaldehyde. Hydroxypivalaldehyde (HPA) and dimethylolbutanal (DMB) are particularly preferred.

Preferred ketones are acetone, butanone, 2-pentanone, 3-pentanone, 2-hexanone, 3-hexanone, cyclohexanone, isophorone, methyl isobutyl ketone, mesityl oxide, acetophenone, propiophenone, benzophenone, benzalacetone, dibenzalacetone, benzalacetophenone, 2,3-butanedione, 2,4-pentanedione, 2,5-hexanedione and methyl vinyl ketone.

It is also possible to convert carboxylic acids and derivatives thereof, preferably those having 1-20 C atoms. The following should be mentioned in particular:

carboxylic acids such as formic acid, acetic acid, propionic acid, butyric acid, isobutyric acid, n-valeric acid, trimethylacetic acid ("pivalic acid"), caproic acid, enanthic acid, caprylic acid, capric acid, lauric acid, myristic acid, palmitic acid, stearic acid, acrylic acid, methacrylic acid, oleic acid, elaidic acid, linoleic acid, linolenic acid, cyclohexane-carboxylic acid, benzoic acid, phenylacetic acid, o-toluic acid, m-toluic acid, p-toluic acid, o-chlorobenzoic acid, p-chlorobenzoic acid, o-nitrobenzoic acid, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid;

carboxylic esters such as the $C_1$-$C_{10}$-alkyl esters of the abovementioned carboxylic acids, in particular methyl formate, ethyl acetate, butyl butyrate, dialkyl phthalates, isophthalates, terephthalates, adipates, maleates such as the dimethyl esters of these acids, methyl (meth)acrylate, butyrolactone, caprolactone and polycarboxylic esters such as polyacrylic and polymethacrylic esters and their copolymers and polyesters such as polymethylmethacrylate, terephthalic esters and other engineering plastics, in this case hydrogenolysis, i.e. the conversion of esters to the corresponding acids and alcohols, being carried out in particular;

fats;

carboxylic anhydrides such as the anhydrides of the above-mentioned carboxylic acids, especially acetic anhydride, propionic anhydride, benzoic anhydride and maleic anhydride;

carboxamides such as formamide, acetamide, propionamide, stearamide, terephthalamide.

It is also possible to convert hydroxy carboxylic acids such as lactic, malic, tartaric or citric acid, or amino acids such as glycine, alanine, proline and arginine, and peptides.

Organic compounds which are particularly preferably hydrogenated are saturated or unsaturated carboxylic acids, carboxylic esters, carboxylic anhydrides or lactones or mixtures of two or more thereof.

Accordingly, the present invention also relates to a process as described above, wherein the organic compound is a carboxylic acid, a carboxylic ester, a carboxylic anhydride or a lactone.

Examples of these compounds are, inter alia, maleic acid, maleic anhydride, succinic acid, succinic anhydride, adipic acid, 6-hydroxycaproic acid, 2-cyclododecylpropionic acid, the esters of the aforementioned acids, such as, for example, methyl, ethyl, propyl or butyl esters. Further examples are γ-butyrolactone and caprolactone.

In a very particularly preferred embodiment, the present invention relates to a process as described above, wherein the organic compound is adipic acid or an adipic ester.

The carbonyl compound to be hydrogenated can be fed into the hydrogenation reactor alone or as mixture with the product of the hydrogenation, in which case this can take place in undiluted form or with use of additional solvent. Particularly suitable additional solvents are water, alcohols such as methanol, ethanol and the alcohol produced under the reaction conditions. Preferred solvents are water, THF, and NMP, and water is particularly preferred.

The hydrogenation in both the upflow and the downflow procedure, each preferably being carried out as recycle procedure, is generally carried out at a temperature in the range from 50 to 350° C., preferably in the range from 70 to 300° C., particularly preferably in the range from 100 to 270° C., under a pressure in the range from 3 to 350 bar, preferably in the range from 5 to 330 bar, particularly preferably in the range from 10 to 300 bar.

In a very particularly preferred embodiment, the catalysts of the invention are employed in processes for preparing hexanediol and/or caprolactone, as described in DE 196 07 954, DE 196 07 955, DE 196 47 348 and DE 196 47 349.

High conversions and selectivities are obtained in the process of the invention using the catalysts of the invention. At the same time, the catalysts of the invention show high chemical and mechanical stability.

The present invention therefore relates very generally to the use of Cu—Al catalysts to which lanthanum, tungsten, molybdenum, titanium and/or zirconium oxides have been added during the preparation of a catalyst to increase both the mechanical stability and the activity and selectivity of the catalyst.

In a preferred embodiment, the present invention relates to a use as described above, wherein the catalyst comprises copper as active component.

The mechanical stability of the solid catalysts and specifically of the catalysts of the invention is described by the side crushing strength parameter in various states (oxidic, reduced, reduced and suspended under water).

The side crushing strength was determined for the purposes of the present application using an apparatus of the type "Z 2.5/T 919" supplied by Zwick (Ulm). The measurements were carried out under a nitrogen atmosphere both for the reduced and for the used catalysts in order to avoid reoxidation of the catalysts.

The invention is to be described in more detail in the following examples.

EXAMPLES

Example 1

Preparation of Catalyst 1

Preparation of the Catalyst

A mixture of 12.41 kg of a 19.34% strength copper nitrate solution, and 14.78 kg of an 8.12% strength aluminum nitrate solution and 1.06 kg of a 37.58% strength lanthanum nitrate× $6H_2O$ solution were dissolved in 1.5 l of water (solution 1). Solution 2 comprises 60 kg of a 20% strength anhydrous $Na_2CO_3$. Solution 1 and solution 2 are passed through separate lines into a precipitating vessel which is provided with a stirrer and contains 10 l of water heated to 60° C. Appropriate adjustment of the feed rates of solution 1 and solution 2 during this brought the pH to 6.2.

While keeping the pH constant at 6.2 and the temperature at 60° C., the whole of solution 1 was reacted with sodium carbonate. The suspension thus formed was then stirred for 1 hour, during which the pH is run up to 7.2 by occasional addition of dilute nitric acid or sodium carbonate solution 2. The suspension is filtered and washed with distilled water until the nitrate content of the aqueous washing was <10 ppm.

The filter cake was dried at 120° C. for 16 h and then calcined at 300° C. for 2 h. The catalyst powder obtained in this way is precompacted with 1% by weight graphite. The resulting compact is mixed with 5% by weight Unicoat Cu flakes and then with 2% by weight graphite and compressed to tablets with a diameter of 3 mm and a height of 3 mm. The tablets were finally calcined at 350° C. for 2 h.

The catalyst prepared in this way has the chemical composition 57% $CuO$/28.5% $Al_2O_3$/9.5% $La_2O_3$/5% Cu. The side crushing strengths in the oxidic and reduced state are listed in Table 1.

Example 2

Hydrogenation of Dimethyl Adipate over Catalyst 1

Dimethyl adipate was hydrogenated continuously in a downflow procedure with recycling (feed/recycling ratio=10/1) at a space velocity of 0.3 kg/(l*h), under a pressure of 200 bar and at reaction temperatures of 220° C. and 240° C. in a vertical tube reactor packed with 200 ml of catalyst 1. The experiment lasted a total of 7 days. GC analysis detected in the discharge from the reactor at 220° C. and 240° C. ester conversions of 98-99% and 99%, respectively, and hexanediol contents of 57% and 62%, respectively. After removal, the catalyst was still completely intact and showed high mechanical stability. Side crushing strengths are compiled in Table 1. The experimental results are compiled once again in Table 2.

Example 3

Preparation of the Comparative Catalyst

The comparative catalyst was prepared in analogy to catalyst 1 but without adding the lanthanum nitrate solution, which means: 14.5 kg of a 19.34% strength copper nitrate solution and 14.5 kg of an 8.12% strength aluminum nitrate solution (solution 1) are precipitated with a sodium carbonate solution in analogy to catalyst 1.

The catalyst prepared in this way has the chemical composition 66.5% CuO/28.5% $Al_2O_3$/5% Cu. The side crushing strengths in the oxidic and reduced state are listed in Table 1.

Example 4

Hydrogenation of Dimethyl Adipate over the Comparative Catalyst

Dimethyl adipate was hydrogenated continuously in a downflow procedure with recycling (feed/recycling ratio=10/1) at a space velocity of 0.3 kg/(l*h), under a pressure of 200 bar and at reaction temperatures of 220° C. and 240° C. in a vertical tube reactor packed with 200 ml of catalyst 2. The experiment lasted a total of 7 days. GC analysis detected in the discharge from the reactor at 220° C. and 240° C. ester conversions of 98% in each case and hexanediol contents of 55%. After removal, the catalyst was still completely intact and showed high mechanical stability. Side crushing strengths are compiled in Table 1. The experimental results are compiled once again in Table 2.

TABLE 1

| Catalyst | Side crushing strength (oxidic)/N | Side crushing strength (reduced)/N | Side crushing strength (after removal)/N | Side crushing strength (reduced, suspended under water)/N |
|---|---|---|---|---|
| Catalyst 1 | 111 | 62 | 51 | 41 |
| Comparative catalyst | 70 | 45 | 20 | 26 |

The data in Table 1 show that catalyst 1 of the invention shows a distinctly higher mechanical stability in reduced state and after removal than the comparative catalyst.

The data in Table 2 below show that the catalysts of the invention have significantly higher hydrogenation activities, i.e. higher conversions of dimethyl adipate at 220° C. and 240° C., than the comparative catalyst, and also tend to have higher selectivities for required product, i.e. contents of the target product hexanediol in the discharge.

TABLE 2

| Catalyst | Reaction temperature/° C. | Dimethyl adipate conversion/% | Hexanediol content in discharge/% |
|---|---|---|---|
| Catalyst 1 | 220 | 98 | 57 |
|  | 240 | 99 | 62 |
| Comparative catalyst | 220 | 92 | 48 |
|  | 240 | 96 | 58 |

We claim:

1. A process for hydrogenating an organic compound having at least one carbonyl group, comprising contacting the organic compound comprising at least one carbonyl group in the presence of hydrogen with a shaped article wherein the shaped article is produced in a process comprising:
    preparing an oxidic material comprising copper oxide, aluminum oxide and at least one selected from the group consisting of lanthanum oxide, tungsten oxide, and a mixture thereof, by simultaneous precipitation of the copper oxide, aluminum oxide and at least one of lanthanum oxide, tungsten oxide, and a mixture thereof from a solution of salts of the metals;
    adding at least one substance selected from the group consisting of powdered metallic copper, copper flakes, powdered cement, graphite and a mixture thereof to the oxidic material, and
    shaping the mixture of the oxidic material and at least one substance to the shaped article,
wherein
    the organic compound comprising at least one carbonyl group is selected from the list of compounds consisting of an aldehyde, a ketone, a carboxylic acid, a carboxylic acid ester and a carboxylic acid anhydride.

2. The process according to claim 1, wherein the oxidic material comprises:
    copper oxide;
    aluminum oxide; and
    at least one selected from the group consisting of lanthanum oxide, tungsten oxide, and a mixture thereof;
wherein
    a % by weight content of copper oxide is in the range from 50 to 80%,
    a % by weight content of aluminum oxide is in the range from 15 to 35%,
    a % by weight of the selected lanthanum oxide, tungsten oxide, or mixture thereof is in the range from 2 to 20%, in each case based on the total weight of the oxidic material after calcination, and a total % by weight content of the copper oxide, aluminum oxide and selected lanthanum oxide, tungsten oxide, or mixture thereof is in the range from 80 to 100%, and
wherein cement is not included with the oxidic material in regard to % by weight.

3. The process according to claim 1 or 2, wherein the adding results in addition of the powdered metallic copper, the copper flakes, the powdered cement or graphite or the mixture thereof in a content in the range from 1 to 40% by weight based on the total weight of the oxidic material.

4. The process according claim 1, wherein graphite is added in a content in the range from 0.5 to 5% by weight based on the total weight of the oxidic material to the oxidic material or to the mixture of the oxidic material and at least one lanthanum oxide, tungsten oxide, or mixture thereof.

5. The process according to claim 1, wherein the organic compound having comprising at least one carbonyl group is a carboxylic acid, a carboxylic ester, a carboxylic anhydride or a lactone.

6. The process according to claim 5, wherein the organic compound having at least one carbonyl group is adipic acid or an adipic acid ester.

7. The process according to claim 2, wherein
the % by weight content of copper oxide is in the range from 55 to 75%,
the % by weight content of aluminum oxide is in the range from 20 to 30%,
the % by weight of the selected lanthanum oxide, tungsten oxide, or mixture thereof is in the range from 3 to 15%, and a total % by weight content of the copper oxide, aluminum oxide and selected lanthanum oxide, tungsten oxide, or mixture thereof is in the range from 95 to 100%.

8. The process according to claim 1, wherein the selected oxide is lanthanum oxide.

9. The process according to claim 8, wherein a % by weight content of copper oxide is in the range from 50 to 80%,
a % by weight content of aluminum oxide is in the range from 15 to 35%,
a % by weight of lanthanum oxide is in the range from 2 to 20%, in each case based on the total weight of the oxidic material after calcination, and
a total % by weight content of the copper oxide, aluminum oxide and lanthanum oxide is in the range from 80 to 100%, and
wherein cement is not included with the oxidic material in regard to % by weight.

10. The process according to claim 9, wherein a % by weight content of copper oxide is in the range from 55 to 75%,
a % by weight content of aluminum oxide is in the range from 20 to 30%,
a % by weight of lanthanum oxide is in the range from 3 to 15%, in each case based on the total weight of the oxidic material after calcination, and
a total % by weight content of the copper oxide, aluminum oxide and lanthanum oxide is in the range from 95 to 100%.

11. The process according to claim 8, wherein the adding results in addition of the powdered metallic copper, the copper flakes, the powdered cement or graphite or the mixture thereof in a content in the range from 1 to 40% by weight based on the total weight of the oxidic material.

12. The process according to claim 8, wherein the organic compound having at least one carbonyl group is a carboxylic acid, a carboxylic ester, a carboxylic anhydride or a lactone.

13. The process according to claim 8, wherein the organic compound having a structure comprising at least one carbonyl group is adipic acid or an adipic acid ester.

14. The process according to claim 1, wherein the oxidic material further comprises at least one oxide of a metal selected from the group consisting of Re, Fe, Ru, Co, Rh, Ir, Ni, Pd, and Pt.

15. The process according to claim 14, wherein a % by weight content of the further comprised oxidic material does not exceed 10%.

* * * * *